United States Patent
Clark et al.

(10) Patent No.: US 8,012,434 B2
(45) Date of Patent: *Sep. 6, 2011

(54) ANTI-CLOGGING DEVICE AND METHOD FOR IN-GEL DIGESTION APPLICATIONS

(75) Inventors: Phillip Clark, Wakefield, MA (US); Chris A. Scott, Westford, MA (US); Marc Emerick, Winchester, MA (US); William Kopaciewicz, West Newbury, MA (US); Donald B. Rising, Stow, MA (US)

(73) Assignee: Millipore Corporation, Billerica, MA (US)

( * ) Notice: Subject to any disclaimer, the term of this patent is extended or adjusted under 35 U.S.C. 154(b) by 188 days.

This patent is subject to a terminal disclaimer.

(21) Appl. No.: 12/288,658

(22) Filed: Oct. 22, 2008

(65) Prior Publication Data

US 2009/0081083 A1    Mar. 26, 2009

Related U.S. Application Data

(63) Continuation of application No. 10/154,550, filed on May 24, 2002.

(51) Int. Cl.
*B01L 3/00* (2006.01)

(52) U.S. Cl. ....... 422/552; 422/69; 422/513; 435/288.4; 435/305.2

(58) Field of Classification Search ............ 422/101, 422/102, 551–553, 513, 69; 435/288.4, 288.5, 435/305.2; 210/406, 416.1, 455
See application file for complete search history.

(56) References Cited

U.S. PATENT DOCUMENTS

| | | | |
|---|---|---|---|
| 4,902,481 A | 2/1990 | Clark et al. | 422/101 |
| 5,108,704 A | 4/1992 | Bowers et al. | 422/70 |
| 5,171,537 A | 12/1992 | Wainwright et al. | 422/100 |
| 5,343,909 A | 9/1994 | Goodman | 141/242 |
| 6,048,457 A | 4/2000 | Kopaciewicz et al. | 210/321.6 |
| 6,153,194 A | 11/2000 | Skare et al. | |
| 6,159,368 A | 12/2000 | Moring et al. | 210/321.75 |
| 6,309,605 B1 | 10/2001 | Zermani | |
| 2002/0062017 A1 | 5/2002 | Hecker et al. | 536/25.4 |
| 2002/0182114 A1 | 12/2002 | Ingenhoven et al. | 422/99 |

FOREIGN PATENT DOCUMENTS

EP    1053784    5/2000

(Continued)

OTHER PUBLICATIONS

OA dated Nov. 10, 2009 in co-pending U.S. Appl. No. 10/154,550.

(Continued)

*Primary Examiner* — Jan Ludlow
(74) *Attorney, Agent, or Firm* — Nields, Lemack & Frame, LLC

(57) ABSTRACT

An integrated proteomics sample preparation device and method for in-gel digestion of proteins and for desalting and concentrating samples prior to further analysis such as by MALDI TOF and/or electro-spray ionization (ESI) mass spectrometry. The device in accordance with an embodiment of the present invention includes a plurality of wells in fluid communication with a an outlet or drainage opening containing a three dimensional structure comprising a plurality of sorptive particles entrapped in a porous polymer matrix so as to form a device capable of carrying out solid phase extraction. In a preferred embodiment, the wells are configured so as to prevent a sample carrier present in the wells from clogging the outlet when subjected to a driving force such as vacuum. The device also reduces or eliminates overflowing of a well in the event a drain becomes clogged during automated operation.

17 Claims, 5 Drawing Sheets

FOREIGN PATENT DOCUMENTS

| | | |
|---|---|---|
| EP | 1 151 793 | 11/2001 |
| JP | 2000-515066 | 11/2000 |
| WO | 98/37949 | 9/1998 |
| WO | 98/55233 | 12/1998 |
| WO | 00/25922 | 5/2000 |

OTHER PUBLICATIONS

English translation of Japanese communication dated Jan. 11, 2005.
"Montage In-Gel Digest96 Kit" Millipore Website, 'Online! Feb. 5, 2002, XP002262384.
European Search Report dated Nov. 21, 2003.
European communication dated Aug. 21, 2008.
European communication dated Nov. 25, 2009.
Office Action dated Apr. 3, 2009 in abandoned corresponding U.S. Appl. No. 11/209,410.
Office Action dated Feb. 16, 2011 in corresponding U.S. Appl. No. 10/154,550.
Office Action dated Mar. 9, 2010 in corresponding U.S. Appl. No. 10/154,550.
Final Rejection dated Nov. 10, 2009 in corresponding U.S. Appl. No. 10/154,550.
Office Action dated Mar. 31, 2009 in corresponding U.S. Appl. No. 10/154,550.
Final Rejection dated Jun. 30, 2008 in corresponding U.S. Appl. No. 10/154,550.
Office Action dated Dec. 28, 2007 in corresponding U.S. Appl. No. 10/154,550.
Office Action dated May 30, 2007 in corresponding U.S. Appl. No. 10/154,550.
Final Rejection dated Dec. 12, 2006 in corresponding U.S. Appl. No. 10/154,550.
Office Action dated Jun. 28, 2006 in corresponding U.S. Appl. No. 10/154,550.
Office Action dated Mar. 17, 2006 in corresponding U.S. Appl. No. 10/154,550.
Final Rejection dated Dec. 14, 2005 in corresponding U.S. Appl. No. 10/154,550.
Office Action dated Jun. 28, 2005 in corresponding U.S. Appl. No. 10/154,550.
Notice of Allowance dated Mar. 31, 2011 in corresponding U.S. Appl. No. 10/154,550.

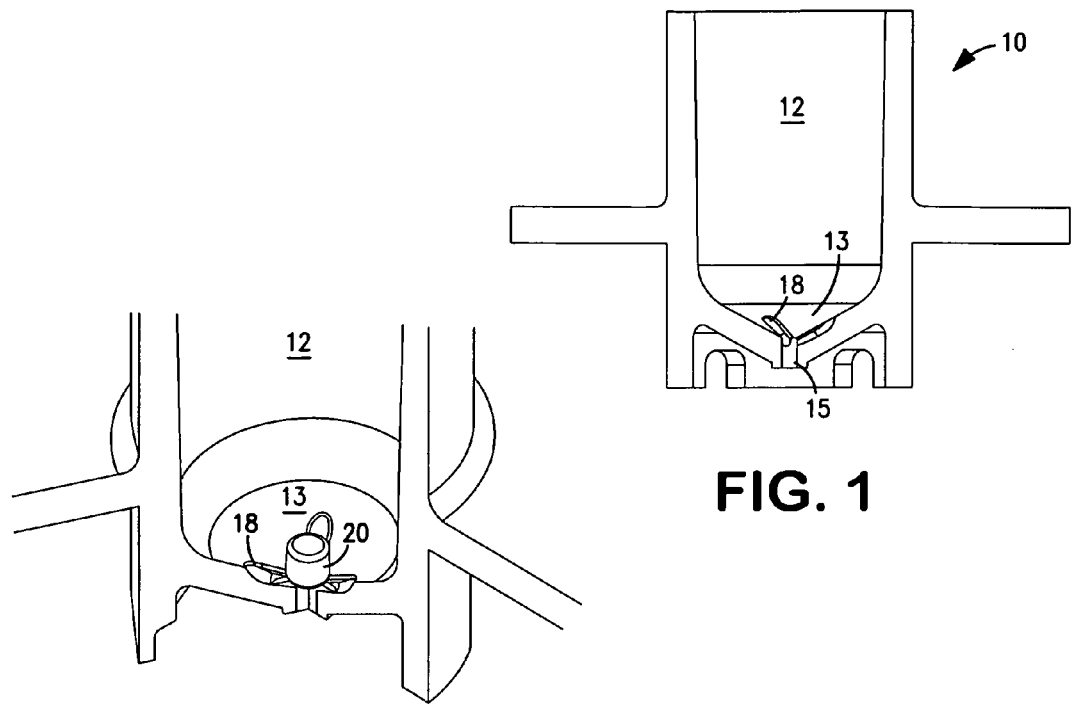
FIG. 1
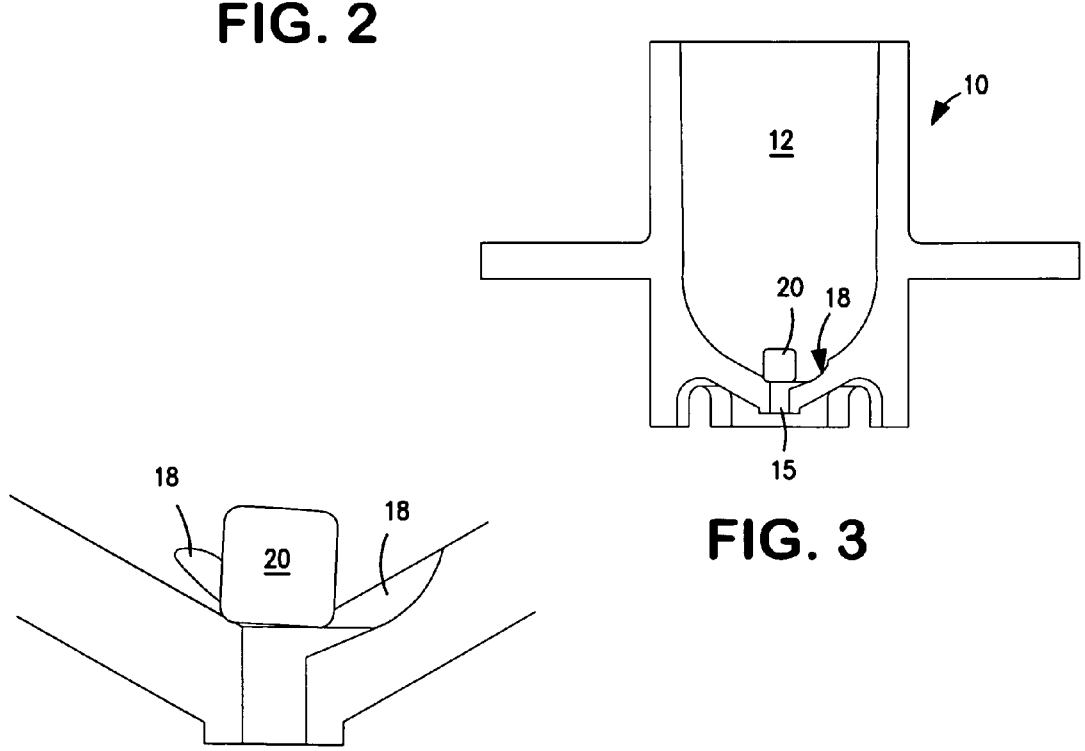
FIG. 2
FIG. 3
FIG. 4

ANTI-CLOGGING DEVICE AND METHOD FOR IN-GEL DIGESTION APPLICATIONS

This application is a continuation of U.S. patent application Ser. No. 10/154,550 filed May 24, 2002, the disclosure of which is incorporated herein by reference

BACKGROUND OF THE INVENTION

Matrix-assisted laser desorption/ionization (MALDI) analysis is a useful tool for solving structural problems in biochemistry, immunology, genetics and biology. Samples are ionized and a time of flight (TOF) analyzer is used to measure ion masses. TOF analysis begins when ions are formed and are accelerated to a constant kinetic energy as they enter a drift region. They arrive at a detector following flight times that are proportional to the square root of their masses. A mass spectrum is created because ions of different mass arrive at the detector at different times.

Mass spectrometry can be a particularly powerful tool in the fields of drug discovery and development, genotyping, and proteome research. Current trends in research are to analyze larger and larger numbers of samples using automated handling equipment or robotics. Quantities of individual samples are from the nano-mole levels to femto-mole levels. As a result, instrumentation is becoming more sensitive and a need exists for sample handling formats to be miniaturized, high density and disposable.

In-gel digestion of protein is a proteomics method that has many sample preparation steps prior to sample analysis (such as by MALDI TOF MS). Briefly, upon separation in the electrophoresis gel, the proteins in a sample are stained for detection and portions of the gel containing the protein of interest are excised. The stain is then removed from these gel portions, and an enzyme solution is used to selectively digest the protein sample to form peptides that migrate out of the gel portion into solution. After purification of the peptides, analysis of the sample is carried out.

Simultaneous preparation and analysis of multiple samples is often desirable. Multiwell plates have been developed for simultaneous assay, typically consisting of 96, 384 or 1536 reaction vessels or wells per plate. It would be desirable to use multiwell plates also for sample handling and preparation, such as the removal of undesired salts and biochemical substances to improve the resolution and selectivity of the mass spectrum.

In this connection, EP 1 151 793 discloses a microtiter plate having lyophobic porous bottoms. Gel pieces containing proteins are placed in the wells of the plate and digested with enzyme. The enzyme is then removed from the gel pieces by centrifugation and applied to a MALDI sample carrier plate for analysis.

However, using centrifugation to bind, wash and elute is a time-consuming process. In addition, it is not easily adaptable to automation or robotics. It would be highly desirable to use the microtiter plate format for enzyme digestion and protein capture that does not require centrifugation, and that is readily adaptable to automation.

Another difficulty is that the gel plugs are deformable and have a similar diameter to the cone-shaped drain outlet of the plate. When vacuum filtered, the gel plugs clog the outlet, causing the well either to not drain or overflow with multiple solution additions, thus contaminating adjacent wells.

It is therefore an object of the present invention to provide a sample preparation method for desalting and purification of samples prior to matrix assisted laser desorption ionization time-of-flight (MALDI TOF) or electro-spray ionization (ESI) mass spectrometry or other analysis methods, that also can be used for digestion of protein, particularly in-gel digestion.

It is a still further object of the present invention to provide a high-density multi-well device wherein various arrays within the device contain chromatographic media having the same or different chemistries, and wherein in-gel digestion of protein is carried out using vacuum as a driving force.

It is a further object of the present invention to provide a sample preparation system and method that is suitable for automated robotics liquid handling equipment.

These and other objects will be made apparent by the following description.

SUMMARY OF THE INVENTION

The problems of the prior art have been overcome by the present invention, one embodiment of which provides an integrated proteomics sample preparation device and method for digestion of proteins and for desalting and concentrating samples prior to further analysis such as by MALDI TOF and/or electro-spray ionization (ESI) mass spectrometry. The device and method of the present invention allows for digestion, desalting and concentration of sample prior to MALDI TOF MS analysis. More specifically, the device in accordance with an embodiment of the present invention includes a plurality of wells each in fluid communication with a respective outlet or drainage opening, optionally containing a three dimensional structure comprising a plurality of sorptive particles entrapped in a porous polymer matrix so as to form a device capable of carrying out solid phase extraction. In a preferred embodiment, the wells are configured so as to prevent a sample carrier, such as a gel piece inserted in the wells from clogging the outlet when subjected to a driving force such as vacuum. The device also reduces or eliminates cross-contamination between wells in the event a drain becomes clogged.

The present invention is also directed towards a method of sample preparation using the device of the present invention.

BRIEF DESCRIPTION OF THE DRAWINGS

FIG. 1 is a perspective view of a single well for a multiwell sample preparation device in accordance with the present invention;

FIG. 2 is a perspective view of a single well for a multiwell sample preparation device shown containing a gel piece in accordance with the present invention;

FIG. 3 is a cross-sectional view of a single well for a multiwell sample preparation device shown containing a gel piece in accordance with the present invention;

FIG. 4 is a enlarged perspective view of a single well for a multiwell sample preparation device shown containing a gel piece in accordance with the present invention;

DETAILED DESCRIPTION OF THE INVENTION

Figure 5:
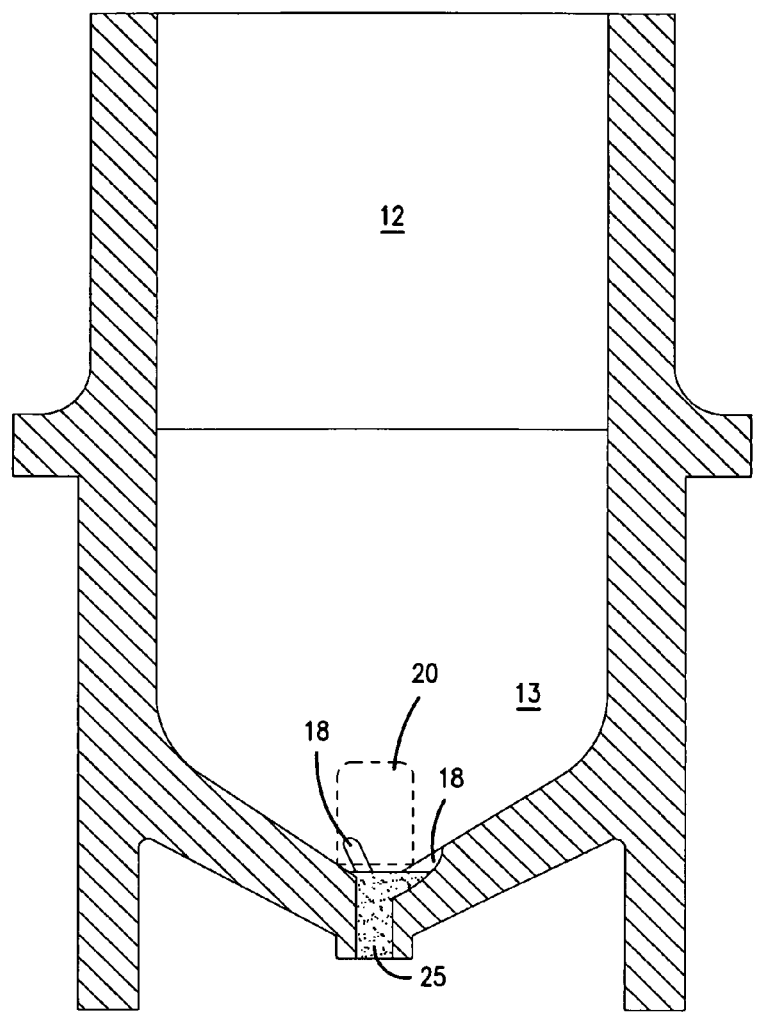
FIG. 5 is a cross-sectional view of a single well for a multiwell sample preparation device shown containing a gel piece (in phantom) and a matrix having adsorptive properties in the drain in accordance with the present invention.

Suitable substrate materials for the sample preparation device of the present invention are not particularly limited, and include plastics (such as polyethylene and polypropylene), glass and stainless steel. The substrate materials should not interfere with the operation of the device or the chemicals to be used in the procedure. Polyolefins, and particularly polypropylene, are preferred materials.

Turning now to FIGS. 1 and 2, there is shown generally at 10 a single well 12 suitable for use in a single well or a multiwell sample preparation device that has a plurality of wells. A well 12 is defined by a vertically extending fluid impervious side wall and a sloping bottom portion. The middle and upper portions of the well 12 preferably have a uniform diameter and are substantially cylindrical in cross-section, although other configurations are contemplated and within the scope of the present invention. The lower portion of the well 12 tapers downwardly, in the direction of fluid flow, towards a bottom portion 13, which slopes inwardly towards a center, thereby having a frusto-conical configuration. Bottom portion 13 has a drain 15 that is preferably centrally located in the well 10.

Formed in the bottom portion 13 of the well 10 are one or more fluid passageways 18. The fluid passageway(s) 18 modify the otherwise relatively smooth or even surface of bottom portion 13 and effectively provide a gap or space between a sample carrier 20, such as a gel piece (FIG. 2), that is contained in well 12 and supported by the bottom portion 13, and the drain 15. The sample carrier can be a liquid but is preferably a solid, such as a gel, coated bead or a membrane. In order to insure fluid flow between the well 12 and drain 15 when the carrier 20 is present in the well 12, the smallest dimension of each passageway 18 should be less than the smallest dimension of the carrier 20, so that the carrier 20 cannot be positioned in the passageway 18 to block fluid flow into the drain 15. In this way, at least a portion of the fluid passageway(s) 18 is always in fluid communication with the drain 15 and cannot be blocked or clogged by a carrier 20 when placed in the well 12, as exemplified by illustration in FIGS. 2, 3 and 4. Where the carrier is a gel piece, it is noted that typically circular plug cutters found in automated picker robots cut the gel portion uniformly. However, the present invention is not limited to uniformly-shaped carriers, as the fluid passageway(s) 18 are configured to prevent fluid blockage even when carriers of irregular shape are present in the well 12. For example, a single slit that is longer than the carrier is within the scope of the present invention.

Figure 5A:
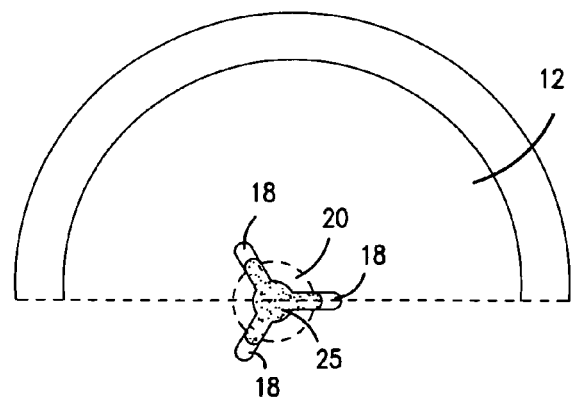
FIG. 5A is a top view of fluid passageways formed in the well in accordance with the present invention.
Figure 7:
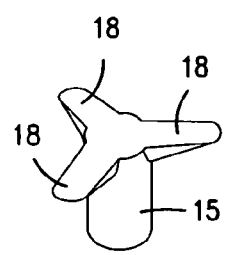
FIG. 7 is a perspective view of a solid rendering of the drain and passageways of a well in accordance with the present invention.

Although a single passageway 18 is sufficient to insure fluid flow around the sample carrier, preferably there is a plurality of such passageways. At least two passageways 18, most preferably three passageways 18, formed symmetrically about the drain 15 as best seen in FIGS. 5A and 7, is the particularly preferred arrangement. The symmetrical arrangement of the passageways about the drain 15 ensure that regardless of the orientation of the carrier 20 in the well 12, fluid communication between the well 12 and the drain 15 will be maintained. The shape and topology of the passageway(s) 18 are not particularly limited, as long as they do not match that of the carrier 20. Preferably the passageway(s) 18 are lobes, but a square, stepped round, cone with a bump or cross bar also are suitable configurations. As best seen in FIG. 7, the lobes preferably taper so that they are deeper as they approach the drain 15.

Figure 9:
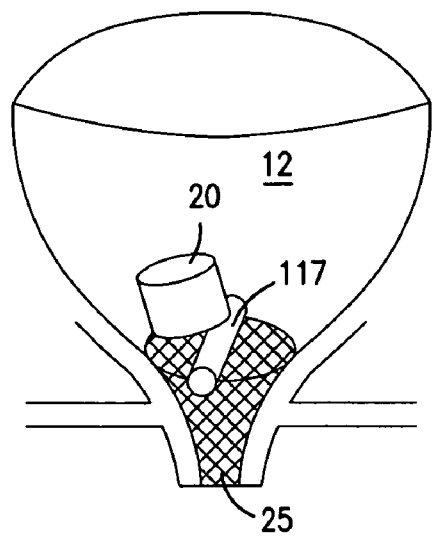
FIG. 9 is a perspective view of a well having a dividing member in accordance with an embodiment of the present invention.
Figure 10:
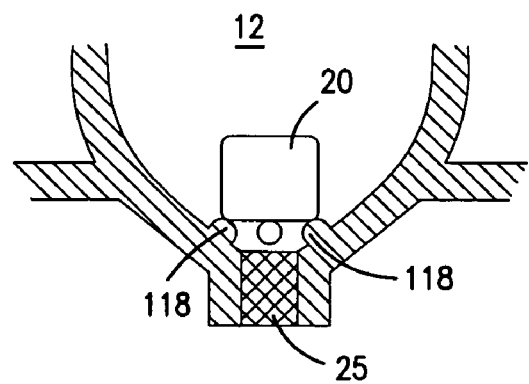
FIG. 10 is a cross-sectional view of a well having raised bumps in accordance with an embodiment of the present invention.

The passageway(s) 18 are preferably formed by creating asymmetry in the surface of the bottom portion 13. This can be accomplished by providing grooves in the surface, or by providing raised portions or protrusions in or on the surface such as a cross bar 117 (FIG. 9) or ribs or bumps 118 (FIG. 10). Preferably the passageways 18 are grooves having a depth of about 0.2 mm, a width of about 0.25 mm and a length of about 1 mm. In the embodiment utilizing protrusions, the protrusions are designed so that the largest opening in the drain is smaller than the smallest dimension of the sample carrier. The objective is to prevent the sample carrier 20 from being situated over the drain 15 in such as way as to block fluid flow to the drain 15.

As seen in FIGS. 1 and 7, the drain 15 is a bore, preferably cylindrical and axially aligned with the central longitudinal axis of the well 12. The drain 15 is in fluid communication with the passageways 18. At least a portion of the drain 15 preferably includes an adsorptive composite structure 25 (FIGS. 5 and 5A). Suitable adsorptive composite structures are cast-in-place polymer bound, particle laden adsorptive membrane structures, such as those comprised of chromatographic beads which have been adhered together with a binder and disclosed in U.S. Pat. No. 6,048,457, the disclosure of which is hereby incorporated by reference. One such preferred structure is a three-dimensional structure comprising a plurality of sorptive particles entrapped in a porous polymer matrix and having an aspect ratio (average diameter to average thickness) of less than about 10, preferably less than about 5. The structure 25 is preferably coterminous with the bottom of the drain 15, and extends into the drain 15, preferably extending through the entire depth of the drain 15 and may extend into the passageway(s) 18 as shown in FIG. 5. Although the composite structure 25 can also completely fill the passageway(s) 18, it is preferred that a portion (preferably the upper half), such as 50%, of the passageway(s) 18 remains devoid of structure 25 to ensure the passageway(s) 18 is not blocked by the carrier 20.

Figure 8:
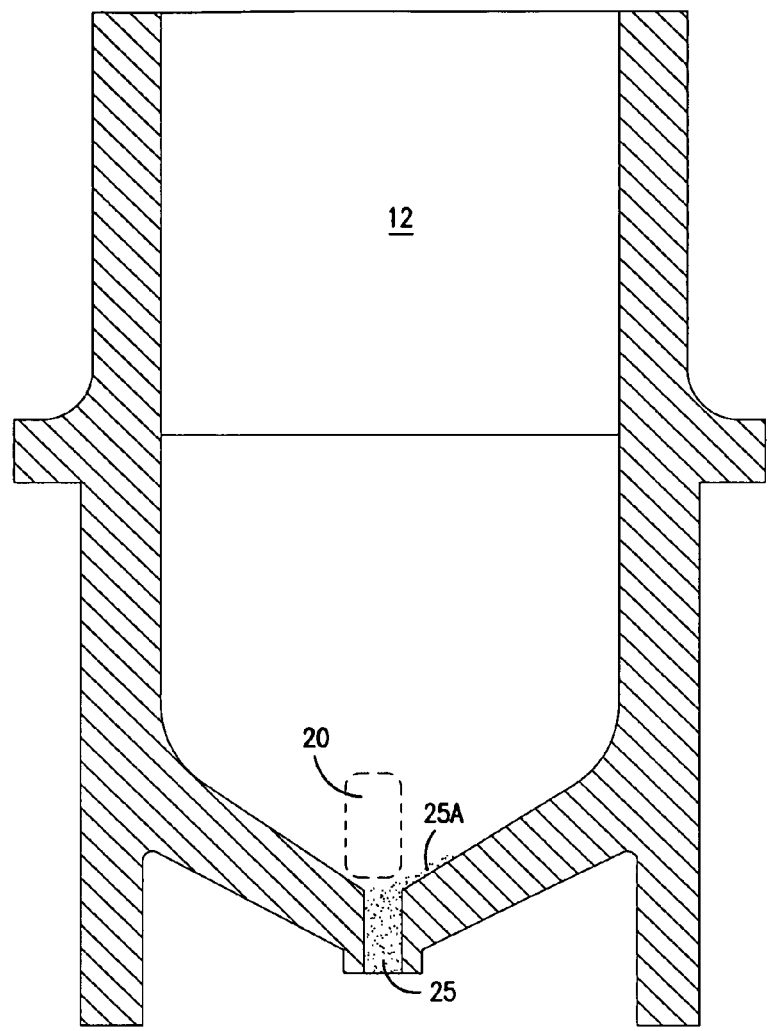
FIG. 8 is a cross-sectional view of a single well for a multiwell sample preparation device shown containing a gel piece (in phantom) and a matrix having adsorptive properties in the drain in accordance with an alternative embodiment of the present invention.
Figure 8A:
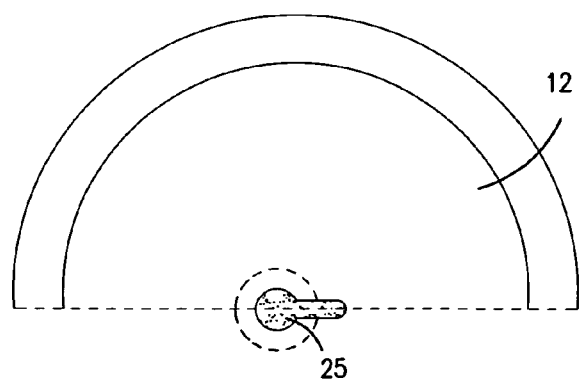
FIG. 8A is a top view of fluid passageways formed in the well in accordance with the embodiment of FIG. 8.

As shown in FIGS. 8 and 8A, the composite structure can be formed to have one or more dimensions that are greater than the largest dimension of the carrier 20, and thus ensure fluid communication between the well and the drain without the formation of a passageway to maintain surface area for flow. For example, the face shape of the composite structure can be a circle having a long leg 25A extending from the circle, or can be in the shape of an eye, thereby ensuring that some surface of the composite structure remains unobstructed and available for flow regardless of the orientation of the carrier 20.

Devices in accordance with the present invention may incorporate a plurality of composite structures having resin materials with different functional groups to fractionate analytes that vary by charge, size, affinity and/or hydrophobicity; alternately, a plurality of devices containing different individual functional membranes may be used in combination to achieve a similar result. Similarly, one or more membranes can be cast in a suitable housing and functionality can be added before or after casting.

In an alternative embodiment, the drain can be devoid of any media, and the device used as a non-clogging processing device that delivers digested proteins to a collection well for analysis or concentration, for example.

After the proteins in the carrier are stained and small pieces of the carrier containing the protein(s) of interest are excised from the site of the stain, each carrier piece is placed in a respective well. A suitable amount of proteolytic enzyme solution is added to each well, such as by pipetting. Sufficient enzyme is added to effectively digest the protein(s). Preferably an excess of enzyme is added, and in sufficient amount to submerge the carrier in each well. After an incubation period to allow the protein digestion to take place and the resulting peptides to diffuse out of the carrier, vacuum is applied to each well, preferably to create a pressure differential of about 5-10 psi, to cause extracted peptides to flow into the drain 15 where they are adsorbed (when media is present) and can then be washed in the conventional manner and freed from buffers, salts and other contaminants. Concentrated peptides then can be eluted and delivered to a suitable target or presentation device for analysis such as by MALDI TOF MS.

Figure 6:
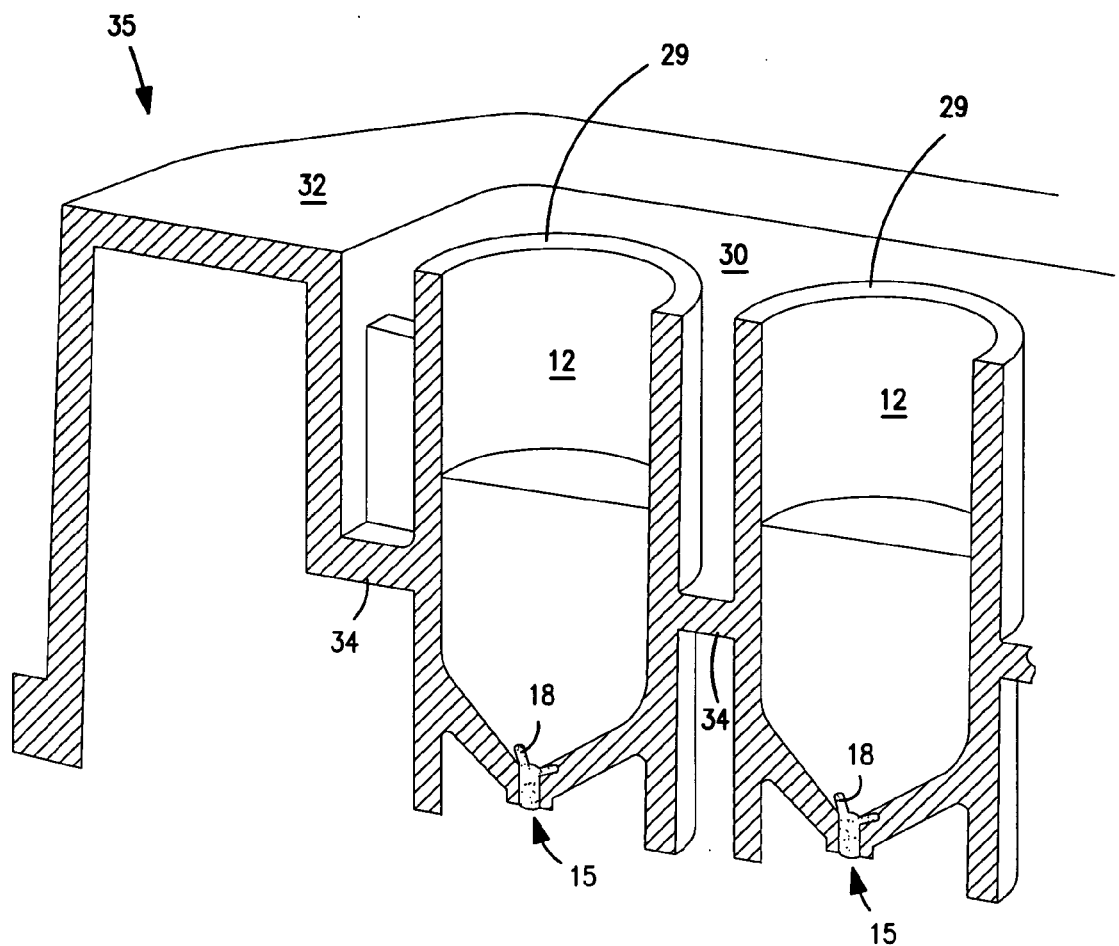
FIG. 6 is a perspective view of two side-by-side wells of a multi-well sample preparation device in accordance with the present invention.

During an automated multi-addition procedure, there is the possibility that wells can overflow, if blocked. The present invention reduces or eliminates the possibility of contamination of other wells as a result of the overflow by incorporating an overflow control feature into the device of the present invention. Specifically, with reference to FIG. 6, surrounding at least a portion of each well 12 is a recess 30. The recess preferably is formed from the top surface 29 of each well 12, which generally corresponds to the top surface 32 of the tray 35, and extends downward (towards the drain 15) about 50% of the length of the well 12, where it terminates in bottom wall 34. The depth of the recess is not critical, as long as is sufficient to contain the overflow volume from at least one well.

What is claimed is:

1. A sample preparation assembly, comprising: a sample carrier, a sample preparation device in which said sample carrier is positioned, said device comprising at least one well having an inlet, a bottom surface, a drain in said bottom surface, and at least one fluid passageway formed in said bottom surface about said drain; said at least one fluid passageway having a dimension smaller than the smallest dimension of said carrier such that fluid communication between said well inlet and said drain, around said sample carrier, is maintained when said carrier is in said well and is positioned on said at least one fluid passageway, said at least one fluid passageway tapering such that it is deeper as it approaches said drain; a source of vacuum in fluid communication with said well; wherein said bottom surface has an inner surface leading to said drain, said inner surface having a center, and wherein said inner surface slopes inwardly towards said center.

2. The assembly of claim 1, wherein said at least one fluid passageway has a dimension less than 1.0 mm.

3. The assembly of claim 1, wherein there are three passageways arranged symmetrically about said drain.

4. The assembly of claim 1, wherein an adsorptive structure is positioned in said drain.

5. The assembly of claim 4, wherein said structure comprises a plurality of sorptive particles entrapped in a porous matrix.

6. The assembly of claim 1, wherein said sample carrier comprises a gel.

7. The assembly of claim 1, wherein there are a plurality of wells.

8. The assembly of claim 7, wherein said plurality of wells are surrounded by a recess.

9. The assembly of claim 1, wherein said inner surface has a frusto-conical configuration.

10. A sample preparation assembly, comprising: a sample carrier, a sample preparation device in which said sample carrier is positioned, said device comprising at least one well having an inlet, a bottom surface, a drain in said bottom surface, and at least one groove formed in said bottom surface about said drain; said at least one groove having a dimension smaller than the smallest dimension of said carrier such that fluid communication between said well inlet and said drain, around said sample carrier, is maintained when said carrier is in said well and is positioned on said at least one groove, said at least one groove tapering such that it is deeper as it approaches said drain; and a source of vacuum in fluid communication with said well; wherein said bottom surface has an inner surface leading to said drain, said inner surface having a center, and wherein said inner surface slopes inwardly towards said center.

11. The assembly of claim 10, wherein there are three grooves arranged symmetrically about said drain.

12. The assembly of claim 10, wherein an adsorptive structure is positioned in said drain.

13. The assembly of claim 12, wherein said structure comprises a plurality of sorptive particles entrapped in a porous matrix.

14. The assembly of claim 10, wherein said sample carrier comprises a gel.

15. The assembly of claim 10, wherein there are at plurality of wells.

16. The assembly of claim 15, wherein said plurality of wells are surrounded by a recess.

17. The assembly of claim 10, wherein said inner surface has a frusto-conical configuration.

* * * * *